(12) United States Patent
Hong et al.

(10) Patent No.: US 11,771,676 B2
(45) Date of Patent: Oct. 3, 2023

(54) METHOD FOR PREPARING HIGH-LOAD ORAL PACLITAXEL CAPSULE FOR SLOW RELEASE IN COLON

(71) Applicant: Jiangnan University, Wuxi (CN)

(72) Inventors: Yan Hong, Wuxi (CN); Beibei Zhao, Wuxi (CN); Zhengbiao Gu, Wuxi (CN); Li Cheng, Wuxi (CN); Zhaofeng Li, Wuxi (CN); Caiming Li, Wuxi (CN); Xiaofeng Ban, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/190,372

(22) Filed: Mar. 27, 2023

(65) Prior Publication Data

US 2023/0233511 A1    Jul. 27, 2023

Related U.S. Application Data

(63) Continuation of application No. PCT/CN2022/133867, filed on Nov. 24, 2022.

(30) Foreign Application Priority Data

Apr. 29, 2022  (CN) .......................... 202210473997.7

(51) Int. Cl.
*A61K 31/337*  (2006.01)
*A61K 9/48*  (2006.01)
*A61K 9/50*  (2006.01)
*A61K 9/00*  (2006.01)

(52) U.S. Cl.
CPC .......... *A61K 31/337* (2013.01); *A61K 9/0053* (2013.01); *A61K 9/4866* (2013.01); *A61K 9/5036* (2013.01)

(58) Field of Classification Search
CPC .. A61K 31/337; A61K 9/0053; A61K 9/4866; A61K 9/5036
See application file for complete search history.

(56) References Cited

U.S. PATENT DOCUMENTS

| | | | |
|---|---|---|---|
| 2002/0041896 A1 | 4/2002 | Straub et al. | |
| 2022/0054425 A1* | 2/2022 | Choi | .................... A61K 31/575 |

FOREIGN PATENT DOCUMENTS

| | | |
|---|---|---|
| CN | 107324308 A | 11/2017 |
| CN | 109044992 A | 12/2018 |
| CN | 114948908 A | 8/2022 |

OTHER PUBLICATIONS

Zhao et al. (CN109044992A Machine Translation) (Year: 2018).*
Xu, Jiaming et. al. "Advances in clinical research of new formulation of paclitaxel" Practical pharmacy and clinical remedies, Apr. 15, 2016, vol. 19, No. 4.

* cited by examiner

*Primary Examiner* — Robert A Wax
*Assistant Examiner* — Quanglong N Truong
(74) *Attorney, Agent, or Firm* — IPRO, PLLC; Na Xu (57) ABSTRACT

Disclosed is a method for preparing high-load oral paclitaxel capsule for a slow release in colon, belonging to the field of porous starch drug loading. The preparation method of the present disclosure includes the following steps: (1) dripping an ethanol solution of paclitaxel into a water phase and drying the solution to obtain an amorphous paclitaxel microsphere; (2) redissolving the paclitaxel microsphere prepared in step (1) in the ethanol solution, dispersing porous starch in the ethanol solution for adsorption, volatilizing a solvent in an oven, washing the porous starch with the ethanol solution to remove unadsorbed paclitaxel, and centrifuging same to obtain a precipitate, namely the porous starch loaded with paclitaxel; and (3) dispersing the porous starch loaded with paclitaxel prepared in step (2) in a chitosan solution, dropwise adding the solution into a phytic acid solution, and stirring the solution for 4 hours to obtain a coated capsule.

9 Claims, 7 Drawing Sheets

METHOD FOR PREPARING HIGH-LOAD ORAL PACLITAXEL CAPSULE FOR SLOW RELEASE IN COLON

TECHNICAL FIELD

The present disclosure relates to the field of porous starch drug loading, in particular to a method for preparing a high-load oral paclitaxel capsule for a slow release in colon.

BACKGROUND

Colon cancer is a common malignancy of the digestive tract, originated from a colonic mucosal epithelium. Colon cancer invades a plurality of internal organs and tissues, seriously injures the body of a patient, and has a relatively high fatality rate. Paclitaxel, a natural anticancer drug, can be used for the treatment of colon cancer. However, the paclitaxel has an extremely poor water solubility. A commonly used clinical injection preparation of the paclitaxel causes a severe allergic reaction and adverse reactions such as toxicity of liver, heart, etc. after injection, and is expensive. An oral administration of the paclitaxel emerges and is expected to improve compliance of a patient. In particular, an oral drug has an advantage of treating gastrointestinal disorders where a concentration should be much higher in the gastrointestinal tract than that administered through a systemic circulation. However, an absorption of the drug in a proximal intestinal tract may prevent a further distal therapeutic concentration, resulting in a poor bioavailability. In particular, the paclitaxel has a poor solubility in water, resulting in an extensive first-pass metabolism after an oral administration. In other words, a drug delivery to a colonic region must be tailored accordingly.

Starch has excellent characteristics of nonimmunity, water solubility, biodegradability and the like, and is widely used in industries of food, medicine and the like. Use of porous starch (PS) is a cleaner strategy for delivering an active substance than other modifiers. The porous starch has a relatively large specific surface area and good adsorption performance, and is often used as adsorbent for easily oxidized substances (such as vitamin A, vitamin C, and docosahexaenoic acid (DHA)) and controlled drugs. These drugs can be better protected in the porous starch and have a longer shelf life and stability. More importantly, these active substances generally require a controlled release. The porous starch has a unique curved channel and exhibits an enzyme-triggered degradability in vivo, such that a guest object can be transported in a controlled-release mechanism. Due to a space limitation, drug molecules are usually present in a microcrystalline form in a cavity, rather than a highly ordered crystal, which greatly enhances their bioavailability and bioactivity. However, (1) drug loading capacity and encapsulation efficiency of the current porous starch are still not ideal; and (2) pure porous starch cannot well resist erosion and degradation of the gastrointestinal tract well, resulting in a large amount of leakage of the drug in an upper digestive tract and failure to reach the colonic region. Therefore, there is a need for a method for preparing a high-load oral paclitaxel capsule for a slow release in colon. In addition, although there are patents that provide improvements to the porous starch loaded with paclitaxel, there are problems that (1) a drug waste is caused due to a high initial paclitaxel concentration, a non-ideal embedding rate, etc.; (2) a chemical residue is caused by an acetone solvent; and (3) a serious leakage of a drug to a colon part causes a serious toxicity to the upper digestive tract. Therefore, it is necessary to provide a process for efficiently loading and slowly releasing paclitaxel in colon.

SUMMARY

A first objective of the present disclosure is to overcome the above mentioned drawbacks. The present disclosure provides a process for preparing a high-load paclitaxel porous starch, which is slowly released in colon after an oral administration. The capsule obtained by the method has a relatively high drug loading capacity and encapsulation efficiency, and protects paclitaxel from reaching the colon to realize a slow release in a colon segment.

To solve the foregoing technical problems, the technical solution used by the present disclosure is as follows:

The present disclosure provides a method for preparing a high-load oral paclitaxel capsule for a slow release in colon, including the following steps:

(1) preparing an amorphous paclitaxel:
dripping an ethanol solution of paclitaxel into a water phase, and stirring uniformly and drying the solution to obtain an amorphous paclitaxel microsphere;

(2) adsorbing paclitaxel with porous starch:
redissolving the paclitaxel microsphere prepared in step (1) in the ethanol solution, dispersing porous starch in the ethanol solution for adsorption, volatilizing a solvent in an oven, washing the porous starch with the ethanol solution to remove unadsorbed paclitaxel, and centrifuging same to obtain a precipitate, namely the porous starch loaded with paclitaxel; and (3) preparing a chitosan-coated capsule:
dispersing the porous starch loaded with paclitaxel prepared in step (2) in a chitosan solution, after dispersing uniformly, dropwise adding the solution into a phytic acid solution, and stirring the solution to obtain a coated capsule.

In one embodiment of the present disclosure, the ethanol is an anhydrous ethanol.

In one embodiment of the present disclosure, a concentration of the paclitaxel in the ethanol solution of paclitaxel in step (1) is 10-20 mg/mL.

In one embodiment of the present disclosure, a volume ratio of the water phase to the ethanol phase in step (1) is (2-4):1.

In one embodiment of the present disclosure, the water phase in step (1) is deionized water.

In one embodiment of the present disclosure, the drying in step (1) is performed at a temperature of 50-55° C. for 6-8 h.

In one embodiment of the present disclosure, a concentration of the paclitaxel in the redissolved solution in step (2) is 10-30 mg/mL.

In one embodiment of the present disclosure, the porous starch in step (2) is enzymatically hydrolyzed porous starch, a total addition amount of an enzyme is 1%-3%, wherein a ratio of an α-amylase to glucosaccharase is 1:(1-3), and an enzymolysis is performed at a temperature of 45-60° C. for 5-7 h.

In one embodiment of the present disclosure, a mass ratio of the porous starch in step (2) to the paclitaxel microsphere (dry weight) is (3-7):1, preferably, a mass ratio of the porous starch to the paclitaxel microsphere (dry weight) is (3-5):1, and most preferably, a mass ratio of the porous starch to the paclitaxel microsphere (dry weight) is 3:1.

In one embodiment of the present disclosure, the adsorption process in step (2) is that the porous starch is dispersed in the paclitaxel redissolved solution and stirred at 37° C. for 3-5 h.

In one embodiment of the present disclosure, the volatilizing of the solvent in step (2) is performed at a temperature of 40-55° C. for 10-20 min.

In one embodiment of the present disclosure, a volume of the detergent ethanol in step (2) is (10-15):1 to that of an original solvent ethanol.

In one embodiment of the present disclosure, the centrifuging in step (2) is performed at 4,000-6,000 r/min for 5-10 min.

In one embodiment of the present disclosure, the chitosan solution in step (3) is an aqueous solution and a concentration of the chitosan is 30-50 mg/mL.

In one embodiment of the present disclosure, an addition amount of the porous starch loaded with paclitaxel in step (3) is (4-6):1 to that of an addition amount (dry weight) of the chitosan.

In one embodiment of the present disclosure, the phytic acid solution in step (3) is an aqueous solution and has a concentration of 1.5 wt %-2.5 wt %.

In one embodiment of the present disclosure, a volume ratio of the phytic acid solution to the chitosan solution in step (3) is (7-10):1.

The present disclosure utilizes the above process to prepare a high-load oral paclitaxel capsule.

A second objective of the present disclosure is use of the high-load oral paclitaxel capsule prepared by the present disclosure in the preparation of a drug for colon cancer.

Beneficial effects of the present disclosure:

(1) The present disclosure uses porous starch to embed paclitaxel, which is assisted with chitosan coating. The method is green and environment-friendly, has a low cost, and is degradable in vivo.

(2) The process used in the present disclosure improves drug loading capacity (30.17±0.15%) and encapsulation efficiency (90.50±0.31%) of the porous starch in size/shape matching, which is important for an expensive anticancer drug. An raw paclitaxel molecule forms an aggregate, presented in a long-strip crystal through an intermolecular hydrogen bond and/or a bridge network after solvent removal. However, paclitaxel precipitated by an anti-solvent is converted to an amorphous microsphere, which is more easily accommodated by starch pores. In particular, the amorphous microsphere more tends to form a molecular state when released from PS, and thus a solubility of the paclitaxel is improved.

(3) The process used by the present disclosure improves the drug loading capacity and encapsulation efficiency of the porous starch in an adsorption capacity. In particular, the current process research of the porous starch for adsorbing the paclitaxel requires a higher initial concentration of paclitaxel. The process has a better encapsulation efficiency and drug loading capacity when reducing an initial concentration of paclitaxel. This depends on an instantaneous increase of a hydrophobic interaction. In the ethanol phase, solvent molecules often embrace each other via hydrogen bonds to form a "cooperative network". A driving force of the "hydrophobic interaction" is generally considered to be an entropy gain produced from a release of a solvent from a hydrophobic gap. An instantaneous volatilization of the solvent accelerates and amplifies the process, such that the surrounding paclitaxel molecules lose a solvent network and are more concentrated on hydrophobic patches of porous starch.

(4) A release behavior of the paclitaxel capsule prepared by the present disclosure is determined by stability of its structure. A special bent pore channel of the porous starch endows a slow-release characteristic. However, the porous starch cannot resist an erosion of an upper digestive tract. A chitosan-phytic acid coating is a second protection of the paclitaxel and endows the capsule with a colon targeting characteristic. Therefore, the obtained paclitaxel capsule is not released in an acidic gastric juice. In a neutral small intestine, a chitosan skeleton is deprotonated, thus a small amount of the surrounding starch is eroded, producing a drug release of 14.98±1.20%, which is far lower than that of 59.60±2.57% of porous starch alone. Since enzymes degrading chitosan and starch exist, a large number of drugs are slowly and continuously released in colonic fluid. A final releasing rate reaches 86.98±2.90%.

DETAILED DESCRIPTION

The exemplary examples of the present disclosure are described below. It should be understood that the examples are only used to better illustrate the present disclosure, rather than to limit the present disclosure.

Porous starch used in the following examples of the present disclosure: a corn starch solution is dispersed in a sodium acetate buffer at a pH of 5.5 to obtain 30% (w/w) of starch milk, 2% (w/w) of an enzyme (α-amylase:saccharifying enzyme=1:2) is added, the mixture is incubated at 50° C. for 6 h, a pH is adjusted to 3.0 to neutralize a system, and the system is incubated for 15 min. The system is centrifuged at 4,000 r/min and washed with deionized water for 3 times. A final sample is dried at 40° C., sieved with a 100-mesh sieve, and stored for later use.

Test Method

1. Encapsulation Efficiency (EE) and Drug Loading Capacity (DL)

A content of paclitaxel in a prepared supernatant is measured at a wavelength of 230 nm with an ultraviolet-visible spectrophotometer. EE and DL are calculated. A relational expression between DL and EE is:

$$EE\ (\%) = (M_{total} - V_{sup} \times C_{sup})/M_{total} \times 100\%$$

$$DL\ (\%) = (M_{total} - V_{sup} \times C_{sup})/W_{pre} \times 100\%$$

$M_{total}$ is an initial amount of paclitaxel (PTX), $V_{sup}$ is a volume of the supernatant, $C_{sup}$ is a concentration of PTX in the supernatant, and $W_{pre}$ is a total weight of a precipitate.

2. Scanning Electron Microscope

Morphologies of particles are observed with an electron microscope and a scanning electron microscope. A dried sample is fixed on a column by using a double-sided adhesive tape, floating powder is blown off, and the sample is plated with gold for 90 s in vacuum. The whole operation is performed under a low vacuum with an accelerated voltage of 15 kV.

3. Confocal Laser Scanning Microscope (CLSM)

Morphologies of paclitaxel-loaded porous starch are observed by using a confocal laser scanning microscope. Paclitaxel is labeled with nile red (0.1 mg/mL of an ethanol solution). Starch is labeled with fluorescein isothiocyanate (FITC; 0.5 mg/mL of an ethanol solution), stained, and placed in a dark place for 12 h.

4. X-Ray Diffraction Measurement

The sample is measured using an X-ray diffractometer. A working power is 2.2 kW, a scanning range is 5°-45°, and a scanning speed is 6°/min.

5. Infrared Determination

A spectrum of the sample is obtained using an FTIR spectrometer. The sample and KBr are completely ground at 1:60. Scanning is performed 32 times at 4,000-400 $cm^{-1}$.

6. Determination of Stability in Upper Digestive Tract and Simulated Colonic Release A simulated gastric fluid (SGF, a pH of 1.2) consists of 2.95 g/L of sodium chloride and 8 ml/L of hydrochloric acid. A paclitaxel capsule (1 mg/ml of paclitaxel (dry weight)) is added to the SGF containing 3.2 g/L of pepsin and placed in a sealed dialysis bag (8,000-14,000 Da), then the dialysis bag is soaked in the SGF containing 3% (v/w) Tween-20 and stirred at 100 rpm at 37±0.5° C., and 2 ml of a release medium is withdrawn at 30 min, 60 min, 90 min, and 120 min respectively. An equal volume of the fresh SGF is added to maintain a volume after each sampling.

A pH value of the SGF system is adjusted to 6.8 with disodium hydrogen phosphate and a fresh porcine trypsin solution at 30 mg/mL is added into the dialysis bag to obtain a simulated intestinal fluid (SIF). 2 ml of a release medium is taken out at 30 min, 60 min, 90 min, and 120 min respectively and a concentration of paclitaxel is determined. An equal volume of the fresh release medium is added to maintain a volume after each sampling.

A pH value of the SIF system is adjusted to 5.5 with sodium dihydrogen phosphate, and 0.8% of a glucosidase and 0.4% of a cellulase (a non-starch polysaccharide degrading enzyme mixture) are added into the dialysis bag to obtain a simulated colonic fluid (SCF). 2 ml of a slow-release solution is taken out at 1 h, 2 h, 3 h, 14 h, 25 h, 36 h, and 40 h respectively and a concentration of paclitaxel is determined. An equal volume of the fresh release medium is added to maintain a volume after each sampling.

The concentration of paclitaxel is measured with an ultraviolet spectrophotometer at a wavelength of 230 nm. The results show a cumulative drug release amount at each time point.

Example 1

A method for preparing a high-load oral paclitaxel capsule for a slow release in colon included the following steps:

(1) Preparing an Amorphous Paclitaxel

Under continuous stirring, an ethanol solution of paclitaxel (20 mg/mL) was dripped into a water phase at 3 times of volume and then the solution was dried at 55° C. to obtain an amorphous paclitaxel microsphere.

(2) Adsorbing Paclitaxel with Porous Starch

The paclitaxel microsphere prepared in step (1) was redissolved in the ethanol solution to form a mixed solution at a concentration of 20 mg/mL. Porous starch was dispersed in the ethanol solution at a mass ratio of the porous starch to the paclitaxel microsphere of 5:1. The solution was stirred at 37° C. for 4 h, and a solvent was volatilized at 40° C. Unadsorbed paclitaxel was removed by washing with the ethanol solution of 10 times volume of the mixed solution to obtain a precipitate, namely the porous starch loaded with paclitaxel.

(3) Preparing a Chitosan-Coated Capsule

The porous starch (600%, w/w) loaded with paclitaxel prepared in step (2) was dispersed in a chitosan solution (5%, w/v, g/mL). After dispersing uniformly, a phytic acid solution (2.5%) of 10 times volume of the chitosan was dropwise added, the solution was stirred for 4 hours and then centrifuged at 3,000 r/min, and a precipitate was placed into an oven at 40° C. to be dried for 6 h to obtain a coated capsule.

The obtained paclitaxel capsule was subjected to a performance test. Test results were as follows: a drug loading capacity of paclitaxel was as high as 17.74±0.05% and an encapsulation efficiency of paclitaxel was as high as 72.20±0.09%. It can be seen in FIG. 2 that a large amount of paclitaxel particles occupied pores of the porous starch, the paclitaxel almost did not release in the stomach, had a release amount of 14.27±1.81% in a small intestine for 4 h and a release amount of 88.91±2.70% in a colonic fluid after 40 h of the release, and achieved an effect of a controlled slow release in colon.

Example 2

A mass ratio of the porous starch to the paclitaxel microsphere in step (2) in example 1 was adjusted to be 3:1. The rest condition was consistent with that in example 1. A high-load oral paclitaxel capsule was obtained.

The obtained paclitaxel capsule was subjected to a performance test. Test results were as follows: a drug loading capacity of paclitaxel was as high as 30.17±0.15% and an encapsulation efficiency of paclitaxel was as high as 90.50±0.31%. It can be seen in FIG. 3 that a large amount of paclitaxel particles occupied pores of the porous starch, the paclitaxel almost did not release in the stomach, had a release amount of 14.98±2.01% in a small intestine for 4 h and a release amount of 83.13±1.25% in a colonic fluid after 40 h of the release, and achieved an effect of a controlled slow release in colon.

Example 3

A mass ratio of the porous starch to the paclitaxel microsphere in step (2) in example 1 was adjusted to be 7:1. The rest condition was consistent with that in example 1. A high-load oral paclitaxel capsule was obtained.

The obtained paclitaxel capsule was subjected to a performance test. Test results were as follows: a drug loading capacity of paclitaxel was as high as 14.20±0.11% and an encapsulation efficiency of paclitaxel was as high as 81.20±0.33%. It can be seen in FIG. 4 that a large amount of paclitaxel particles occupied pores of the porous starch, the paclitaxel almost did not release in the stomach, had a release amount of 14.46±0.31% in a small intestine for 4 h and a release amount of 81.98±2.05% in a colonic fluid after 40 h of the release, and achieved an effect of a controlled slow release in colon.

Example 4

An added ratio of the porous starch to the paclitaxel in step (2) in example 1 was adjusted to be 1:1. The rest condition was consistent with that in example 1. A high-load oral paclitaxel capsule was obtained.

The obtained paclitaxel capsule was subjected to a performance test. Test results were as follows: a drug loading capacity of paclitaxel was as high as 30.72±0.71% and an encapsulation efficiency of paclitaxel was only 42.90±0.24%, indicating that a drug loading space of the porous starch was saturated.

Comparative Example 1 Raw Paclitaxel

Raw paclitaxel was directly subjected to a simulated release experiment.

Comparative Example 2 Direct Adsorbing of Paclitaxel with Porous Starch

Raw paclitaxel was dissolved in an ethanol solution (20 mg/mL), porous starch was dispersed in the ethanol solution at a mass ratio of the porous starch to the paclitaxel microsphere of 6:1, and the solution was stirred at 37° C. for 4 h and centrifuged at 4,000 r/min for 10 min to obtain a precipitate, namely the porous starch loaded with paclitaxel.

Figure 5:
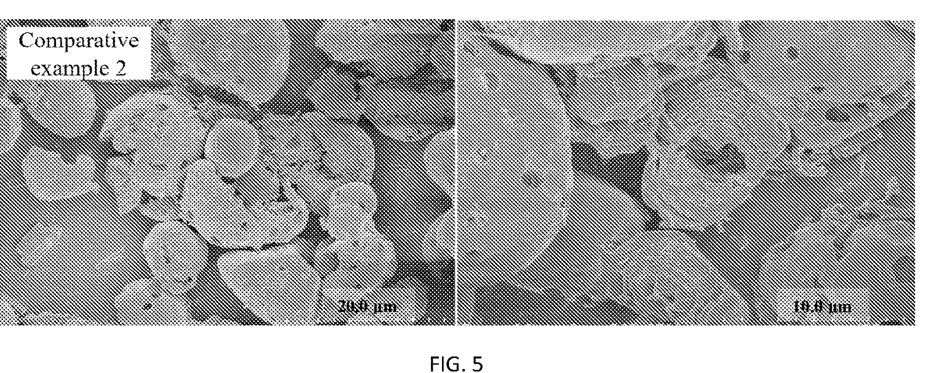
FIG. 5 shows electron microscope images of the paclitaxel capsule prepared in comparative example 2.
Figure 6:
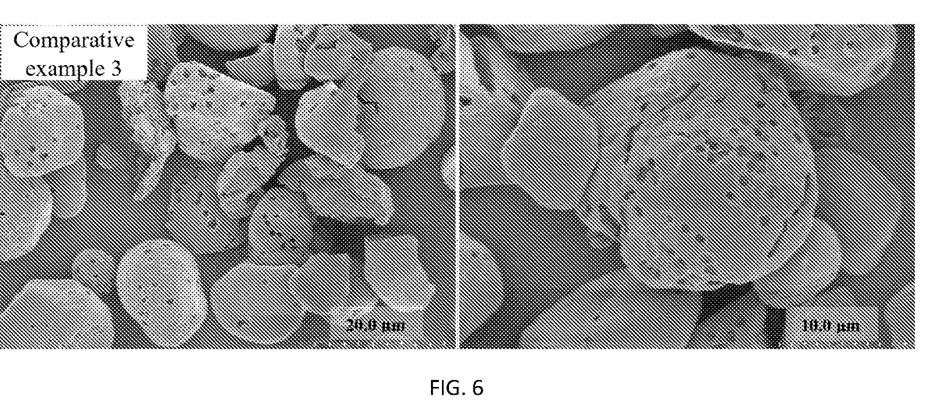
FIG. 6 shows electron microscope images of the paclitaxel capsule prepared in comparative example 3.
Figure 7:
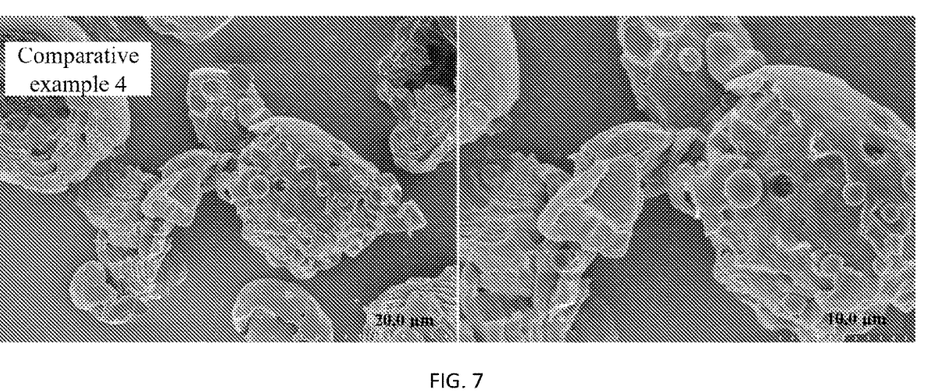
FIG. 7 shows electron microscope images of the paclitaxel capsule prepared in comparative example 4.
Figure 8:
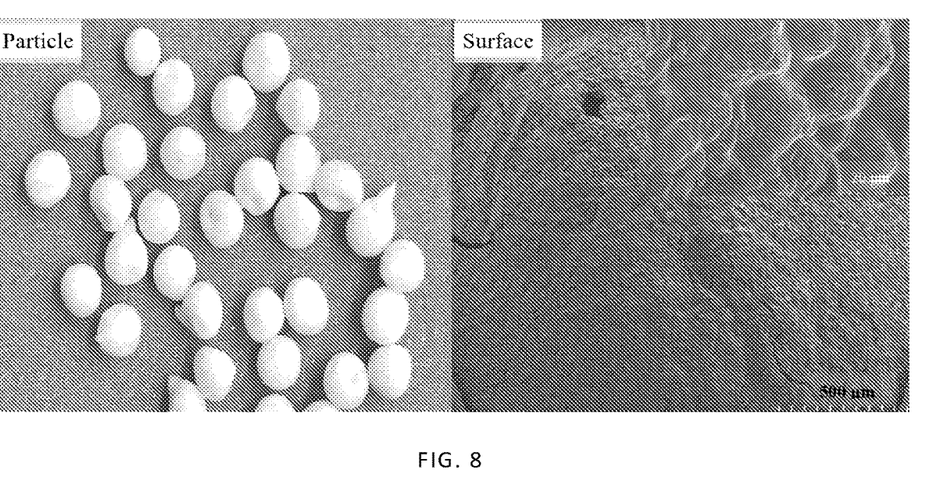
FIG. 8 shows morphologies of a particle of the paclitaxel capsule.

The obtained porous starch loaded with paclitaxel was subjected to a performance test. Test results were as follows: a drug loading capacity of paclitaxel was only 5.20±0.25% and an encapsulation efficiency of paclitaxel was only 30.10±0.13%. It can be seen in FIG. 5 that a small amount of paclitaxel strip crystals occupied surfaces of the porous starch and the paclitaxel had a release amount as high as 59.60±0.60% in a stomach-small intestine.

Comparative Example 3

Menthone was dissolved in an ethanol solution (20 mg/mL), porous starch and paclitaxel microsphere were dispersed in the ethanol solution at a mass ratio of 3:1, and the solution was stirred at 37° C. for 4 h and centrifuged at 4,000 r/min for 10 min to obtain a precipitate, namely the porous starch loaded with paclitaxel.

The obtained porous starch loaded with paclitaxel was subjected to a performance test. Test results were as follows: a drug loading capacity of paclitaxel was only 5.13±0.05% and an encapsulation efficiency of menthone was only 15.39±0.22%. No change was observed under a scanning electron microscope.

Comparative Example 4

Paclitaxel was dissolved in an ethanol solution (20 mg/mL). Porous starch was dispersed in the ethanol solution at a mass ratio of the porous starch to the paclitaxel microsphere of 3:1. The solution was stirred at 45° C. for 90 min. Then a porous starch suspension absorbed with the paclitaxel solution was added into deionized water containing poloxamer at a volume ratio of 1:20 drop by drop. The solution was stirred for 130 min. Finally, the porous starch loaded with paclitaxel was separated by filtration and dried to obtain a precipitate, namely the porous starch loaded with paclitaxel.

The obtained porous starch loaded with paclitaxel was subjected to a performance test. Test results were as follows: a drug loading capacity of paclitaxel was only 7.17±0.05% and an encapsulation efficiency was only 21.50±0.12%. Only a few paclitaxel particles were observed under a scanning electron microscope.

Figure 1:
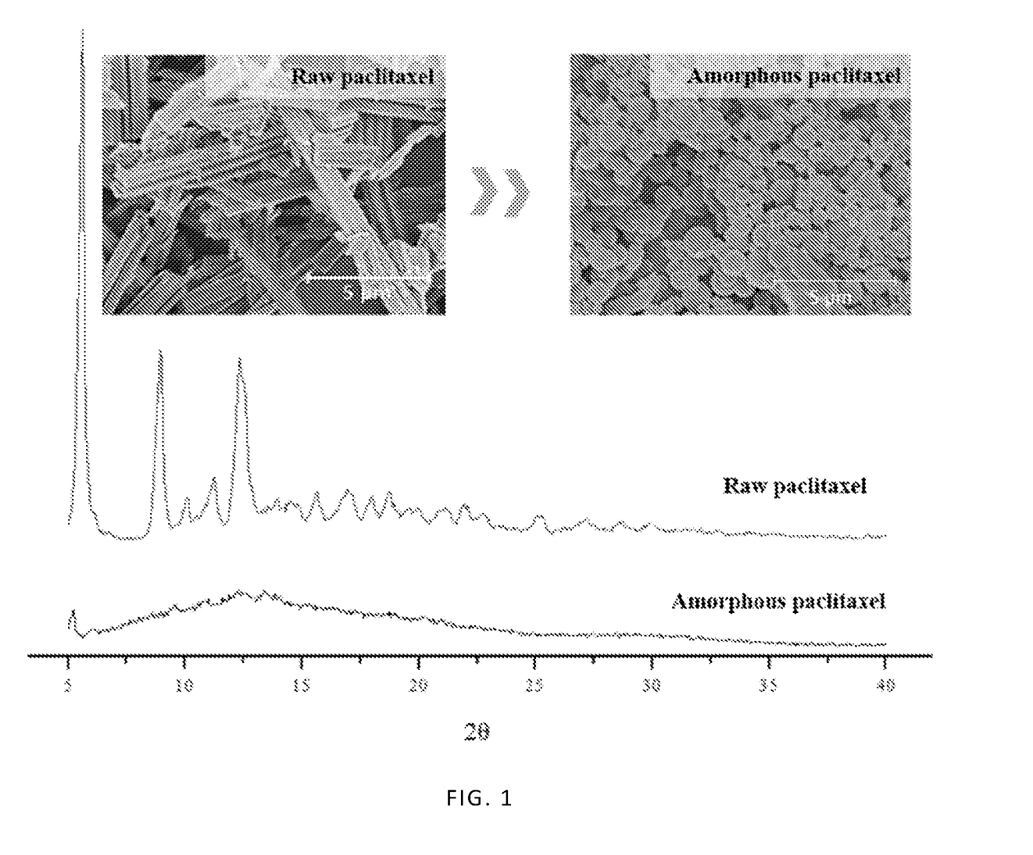
FIG. 1 shows diffractions and morphologies of raw paclitaxel and amorphous paclitaxel.

As shown in FIG. 1, paclitaxel underwent a great change after precipitation by an anti-solvent. A diffraction pattern was amorphous, rather than a crystal structure of the raw paclitaxel. An appearance was spherical with a diameter less than 1 μm, rather than a strip crystal of the raw paclitaxel.

Figure 2:
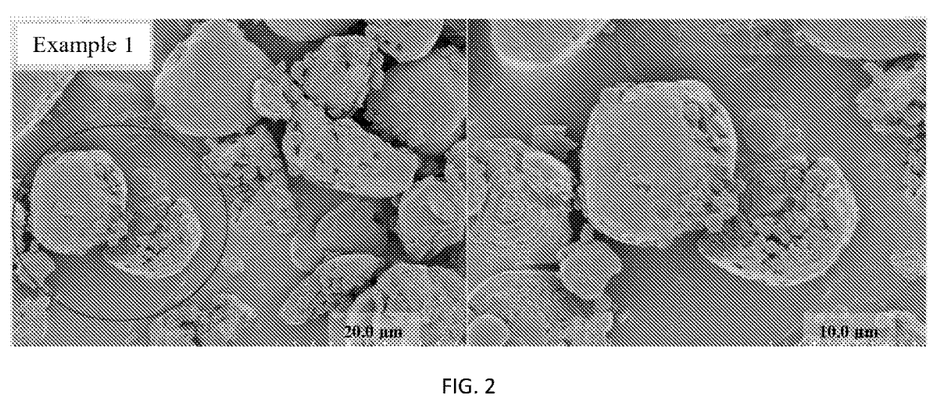
FIG. 2 shows electron microscope images of the paclitaxel capsule prepared in example 1.
Figure 3:
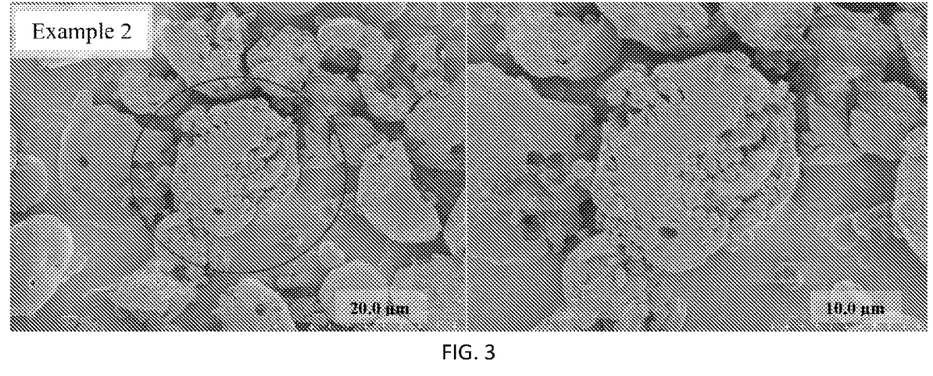
FIG. 3 shows electron microscope images of the paclitaxel capsule prepared in example 2.
Figure 4:
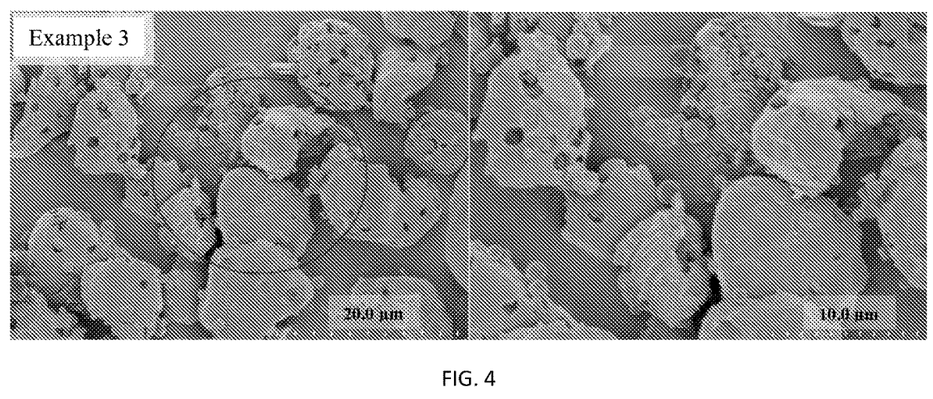
FIG. 4 shows electron microscope images of the paclitaxel capsule prepared in example 3.

Electron microscope images of the paclitaxel capsules prepared in examples 1, 2, and 3 were shown in FIGS. 2-4. The paclitaxel microspheres of examples 1, 2, and 3 were stacked in pores of porous starch and a small amount of the paclitaxel microspheres were attached on a surface of the porous starch. However, the directly adsorbed paclitaxel in comparative example 2 was not found in the pores and only a small amount of irregular debris was shown on the surface. This was consistent with their DL. In addition, when an addition ratio of starch in example 4 was decreased, although a higher loading capacity was obtained, an encapsulation efficiency was too low, indicating that the drug loading of the porous starch was saturated. In fact, the process was tailored to a target paclitaxel. When an adsorption was performed with menthone as a core material in comparative example 3, an effect as the paclitaxel was not obtained. Besides, referring to the prior art, in comparative example 4, an initial concentration was set to be 20 mg/mL, an obtained drug loading capacity was only 7.17±0.05%, and an encapsulation efficiency was only 21.50±0.12%, and particularly, only a small amount of paclitaxel particles were observed on the porous starch under a scanning electron microscope, which indicated that the process of the present disclosure was extremely advantageous.

Figure 9:
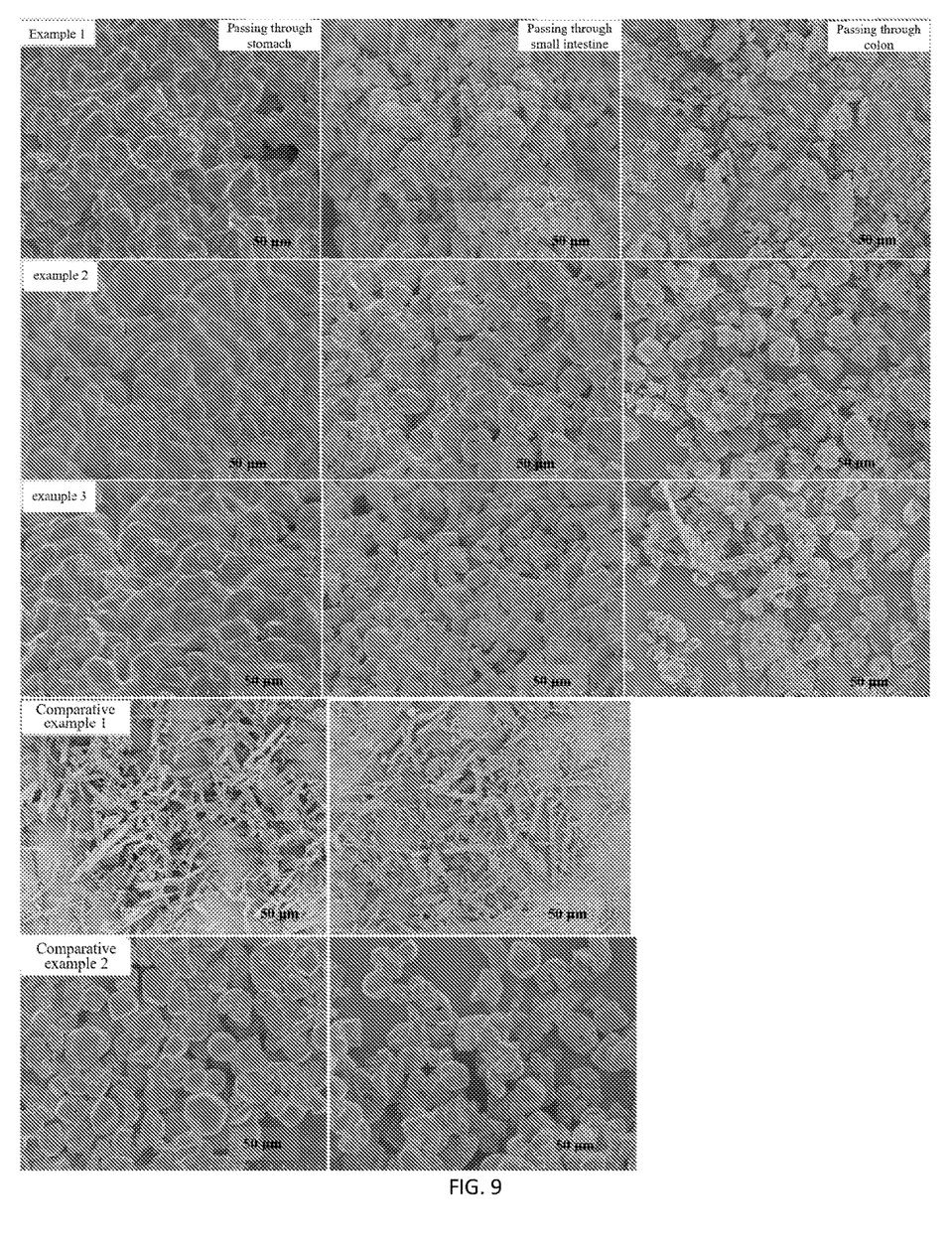
FIG. 9 shows morphologies of the paclitaxel capsules prepared in examples 1, 2, and 3 and samples in comparative examples 1 and 2 after passing through different stages of a digestive tract.
Figure 10:
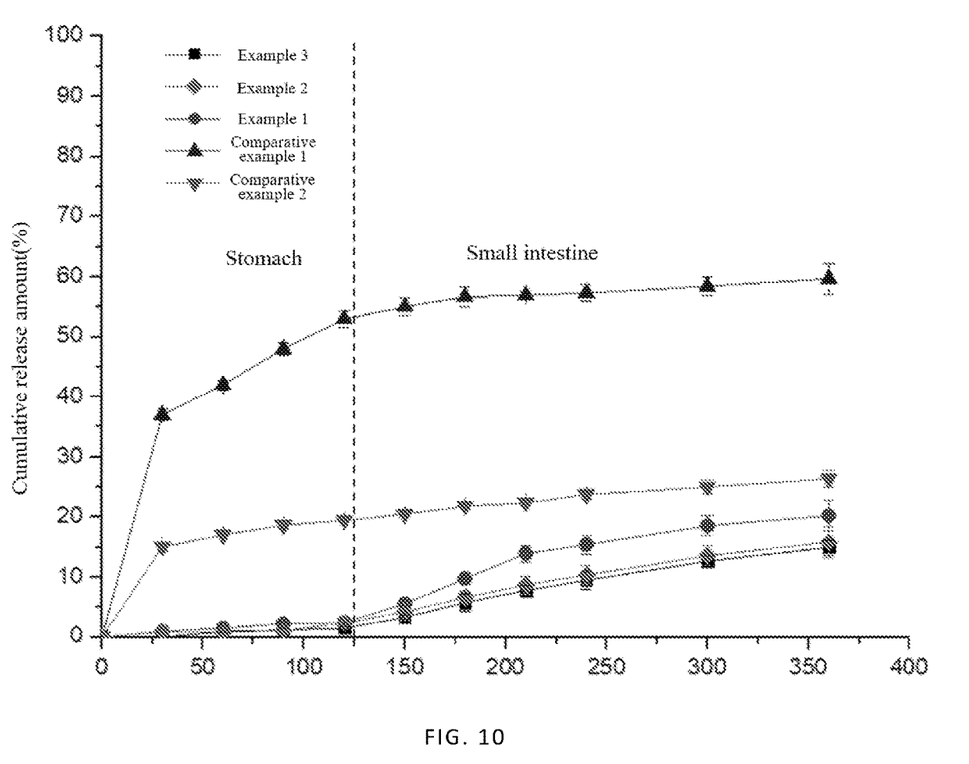
FIG. 10 shows a released amount of paclitaxel of the paclitaxel capsules prepared in examples 1, 2, and 3 and samples in comparative examples 1 and 2 after passing through an upper digestive tract.

As shown in FIG. 3, the paclitaxel capsules of examples 1, 2, and 3 were spherical particles with tightly packed outer shells and a large amount of porous starch loaded with drug inside. Release results in FIG. 10 showed that there was almost no leakage of the capsules during a transportation process in the stomach. However, the direct adsorption in comparative example 2 showed that 53% of paclitaxel was dissolved out. Scanning electron microscope images of FIG. 9 separately showed intact capsule morphologies of the examples and damaged porous starch surfaces of the comparative examples. Furthermore, when the capsules reached a small intestine containing trypsin, a dissolution rate of the capsules of the examples in the small intestine was 14-15%. At this time, the drug-loaded porous starch at an edge of a chitosan skeleton was gradually eroded into debris attached to a periphery of the capsule. However, the samples of the examples cannot resist an erosion of an intestinal fluid and the dissolution rate reached 59.65%. This indicated that a chitosan coating had a better protective effect on paclitaxel. In addition, the dissolution rate of the raw paclitaxel was only about 25% after the raw paclitaxel was digested in the stomach and small intestine, which indicated that the crystalline paclitaxel was not easy to dissolve, but an existence of the porous starch reversed the situation.

Figure 11:
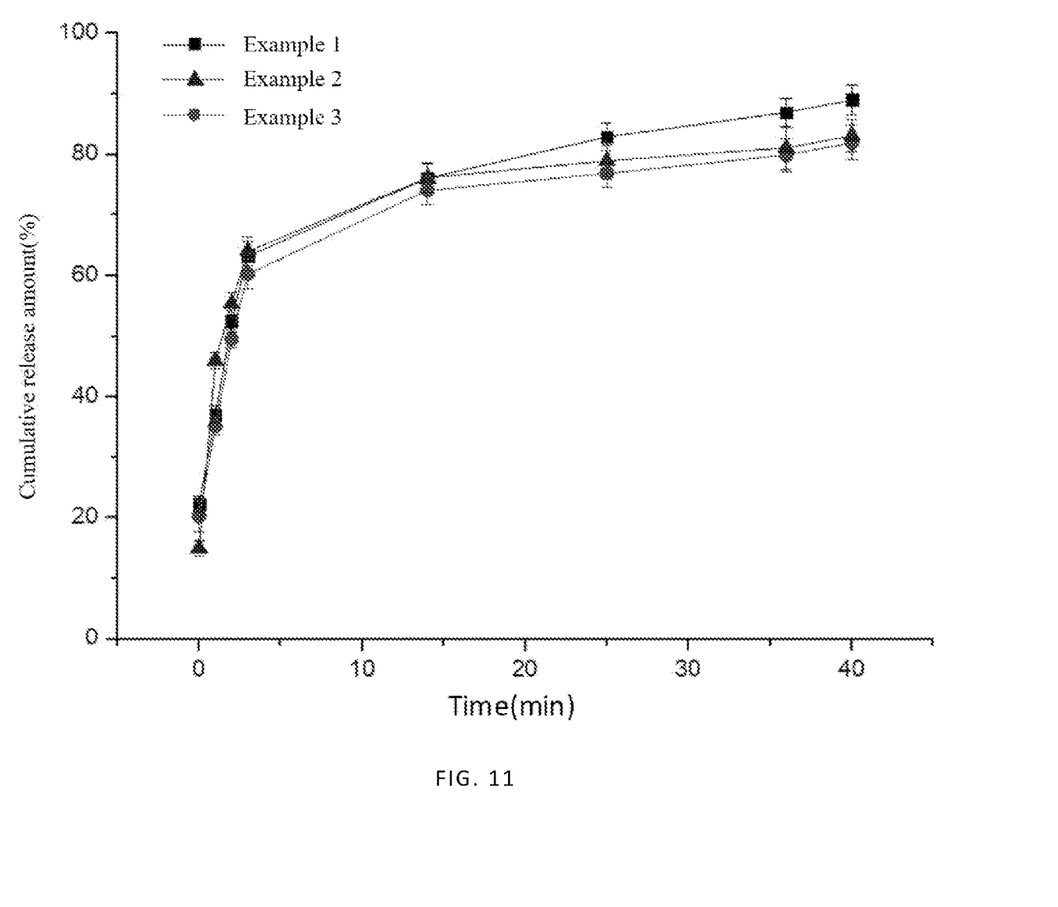
FIG. 11 shows a released amount of paclitaxel of the paclitaxel capsules prepared in examples 1, 2, and 3 in colon.

A colonic microflora secreted multiple types of enzymes. α-glucosidase and a non-starch polysaccharide-degrading enzyme were used herein as disintegrants for the capsules reaching a colon segment. As shown in release curves (FIG. 11), a large amount of the paclitaxel was stably released from the capsules and the final dissolution rate of the drug reached 82-89%. Residues under a scanning electron microscope (FIG. 9) showed that the skeleton of the capsules in the examples was severely damaged and a large amount of degraded starch debris were left.

What is claimed is:

1. A method for preparing a high-load oral paclitaxel capsule for slow release in colon, comprising the following steps:
   (1) preparing an amorphous paclitaxel:
   dripping an ethanol solution of paclitaxel into a water phase, and stirring uniformly and drying the solution to obtain an amorphous paclitaxel microsphere;
   (2) adsorbing paclitaxel with porous starch:
   redissolving the amorphous paclitaxel microsphere prepared in step (1) in the ethanol solution, dispersing porous starch in the ethanol solution for adsorption, volatilizing a solvent in an oven, washing the porous starch with the ethanol solution to remove unadsorbed paclitaxel, and centrifuging same to obtain a precipitate, namely the porous starch loaded with paclitaxel; and
   (3) preparing a chitosan-coated capsule:
   dispersing the porous starch loaded with paclitaxel prepared in step (2) in a chitosan solution, after dispersing uniformly to obtain a solution, dropwise adding the solution into a phytic acid solution, and stirring to obtain a coated capsule.

2. The method according to claim 1, wherein a concentration of the paclitaxel in the ethanol solution of paclitaxel in step (1) is 10-20 mg/mL.

3. The method according to claim 1, wherein a volume ratio of the water phase to the ethanol phase in step (1) is (2-4):1.

4. The method according to claim 1, wherein a mass ratio of the porous starch to the paclitaxel microsphere in step (2) is (3-7):1.

5. The method according to claim 1, wherein the volatilizing of the solvent is performed at a temperature of 40-55° C. for 10-20 minutes in step (2).

6. The method according to claim 1, wherein a mass ratio of the porous starch loaded with paclitaxel to the chitosan in step (3) is (4-6):1.

7. The method according to claim 1, wherein a volume ratio of the phytic acid solution to the chitosan solution in step (3) is (7-10):1.

8. The method according to claim 1, wherein the chitosan solution in step (3) is an aqueous solution at a chitosan concentration of 30-50 mg/mL.

9. A high-load oral paclitaxel capsule prepared by the method according to claim 1.

* * * * *